US006284500B1

(12) United States Patent
Kanzaki et al.

(10) Patent No.: US 6,284,500 B1
(45) Date of Patent: *Sep. 4, 2001

(54) MICROORGANISM RESISTANT TO THREONINE ANALOGUE AND PRODUCTION OF BIOTIN

(75) Inventors: Naoyuki Kanzaki, Ibaraki; Tomohiro Kawamoto, Ikeda; Junji Matsui, Suita; Kazuo Nakahama, Nagaokakyo; Ohji Ifuku, Yokohama, all of (JP)

(73) Assignees: Takeda Chemical Industries, Ltd., Osaka; Shiseido Company, Limited, Tokyo, both of (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/414,634

(22) Filed: Oct. 8, 1999

Related U.S. Application Data

(63) Continuation of application No. 08/793,119, filed on Feb. 19, 1997, now Pat. No. 6,020,173.

(30) Foreign Application Priority Data

Nov. 2, 1995 (JP) .................................................... 7-285761

(51) Int. Cl.[7] ........................... C12P 17/18; C12N 15/01; C12N 1/20; C07H 21/02; C07H 21/04
(52) U.S. Cl. ...................... 435/119; 435/441; 435/252.3; 435/252.33; 536/23.1; 536/23.2
(58) Field of Search ...................................... 435/119, 441, 435/252.3, 252.33; 536/23.1, 23.2

(56) References Cited

U.S. PATENT DOCUMENTS

| 5,110,731 | 5/1992 | Fisher ................................... 435/119 |
| 5,374,554 | 12/1994 | Komatsubara et al. .......... 435/252.3 |
| 5,693,504 | * 12/1997 | Kanzaki et al. ..................... 435/119 |

FOREIGN PATENT DOCUMENTS

| 0 532 426 | 3/1993 | (EP) . |
| 0 635 572 | 1/1995 | (EP) . |
| 9408023 | * 4/1994 | (WO) . |

OTHER PUBLICATIONS

D. Sengupta et al., Biotech. Letters, vol. 17, No. 6, pp. 567–570.

Max Eisenberg, "Regulation of the Biotin Operon in *E. coli*", Annals of the New York Academy of Sciences, vol. 447, pp. 335–349, 1985.

Chattopadhyay, M. et al., Biotech. Letterrs, vol. 17, No. 6, pp. 567–570, Jun. 1995.*

* cited by examiner

*Primary Examiner*—Ponnathapu Achutamurthy
(74) *Attorney, Agent, or Firm*—Wenderoth, Lind & Ponack, L.L.P.

(57) ABSTRACT

A microorganism resistant to a threonine analogue, which has a plasmid containing part or whole of a biotin operon; and a process for producing biotin, which comprises culturing a microorganism described above in a medium to produce and accumulate biotin in the medium, and collecting biotin.

9 Claims, 2 Drawing Sheets

FIG. 1

```
                                                                                      -30
           -80          -70          -60          -50          -40          •
            •            •            •            •            •          AATTAACAACA
r strand→CGTCCGTTGTCATAATCGACTTGTGTAAACCAAATTGAAAAGATTTAGGTTACAAGTCTACACCGAATTAACAACA
l strand→GCAGGCAACAGTATTAGCTGAACATTGGTTTAACTTTTCTAAATCCAATGTTCAGATGTGGCTTAATTGTTGT
                      →
                bioA initiation codon bioB initiation codon
                                                ↑
                                    -10          1           10
                                     •           •            •
AAAAACACGTTTGGAGAAGCCCCATGGCTCACCGCCCA ← r strand
TTTTGTGCAAACCTCTTCGGGGTACCGAGTGGCGGGT ← l strand
       -20
        •
```

MICROORGANISM RESISTANT TO THREONINE ANALOGUE AND PRODUCTION OF BIOTIN

This application is a continuation of Ser. No. 08/793,119 filed Feb. 19, 1997, now U.S. Pat. No. 6,020,173.

FIELD OF THE INVENTION

The present invention relates to a novel microorganism resistant to a threonine analogue and a process for producing biotin using the microorganism. The biotin obtainable by the invention can be used as a raw material for medicaments or cosmetics, feed additives, etc.

BACKGROUND OF THE INVENTION

Biotin (vitamin H) is a kind of vitamin B and is related to fatty acid synthesis or saccharide metabolism as a coenzyme of a carboxylase. About 10 tons of biotin has been produced by chemical synthesis processes every year for use as a raw material for medicaments or cosmetics, feed additives, etc. However, because these processes are complicated, biotin is very expensive. On the other hand, biotin production by fermentation processes has been studied for a long time. The fermentation processes have not become practical because their productivity is low.

Biotin production using gene manipulation techniques has been expected to provide inexpensive biotin. Some microorganisms modified by gene engineering techniques have been used for biotin production. For example, microorganisms belonging to the genus Escherichia such as a strain resistant to α-dehydrobiotin disclosed in e.g. JP-A 61-149091 are known as the modified microorganisms for the biotin production. Other known modified microorganisms for the biotin production include microorganisms belonging to the genus Bacillus modified by transforming *Bacillus sphaericus* and then providing resistance to thenoyltrifluoroacetone (JP-A 4-11894), microorganisms belonging to the genus Serratia modified by providing *Serratia marcescens* SB411 with ethionine-resistance followed by S-aminoethylcysteine-resistance and then transforming the resulting microorganism with a recombinant plasmid containing a biotin gene fragment (JP-A 5-199867), transformants of *Serratia marcescens* SB411 provided with resistance to actithiazic acid, a compound having biotin-like structure, or resistance to 5-(2-thienyl)-n-valeric acid (JP-A 2-27980), and transformants provided with resistance to a nicotinic acid analogue (Japanese Patent Application No. 6-311778).

However, the prior art processes for producing biotin are unsatisfactory for the industrial production of biotin. There is still a need for a process for producing biotin having increased biotin productivity.

OBJECTS OF THE INVENTION

The main object of the present invention is to provide a microorganism which can produce biotin in high yield.

Another object of the present invention is to provide a process for producing biotin using the above microorganism.

These objects as well as other objects and advantages of the present invention will become apparent to those skilled in the art from the following description with reference to the accompanying drawings.

SUMMARY OF THE INVENTION

S-Adenosylmethionine is essential for the main synthetic pathway from pimelyl CoA to desthiobiotin (a biotin precursor). The present inventors have expected that enhancing the biosynthetic pathway to methionine would enhance the supplying system of S-adenosylmethionine, thereby improving the accumulation of desthiobiotin and biotin.

In order to enhance the biosynthetic pathway to methionine, the present inventors have isolated a strain resistant to a threonine analogue from a biotin-producing microorganism, and obtained a strain with significantly increased desthiobiotin and biotin accumulation. After further studies based on this finding, the present invention has been accomplished.

The present invention provides a microorganism resistant to a threonine analogue, which has a plasmid containing part or whole of a biotin operon.

The present invention also provides a process for producing biotin, which comprises culturing a microorganism described above in a medium to produce and accumulate biotin in the medium, and collecting biotin.

BRIEF DESCRIPTION OF THE DRAWINGS

FIG. 1 shows a regulatory region of the biotin operon and a base sequence near the bio B initiation codon.

DETAILED DESCRIPTION OF THE INVENTION

Figure 2:
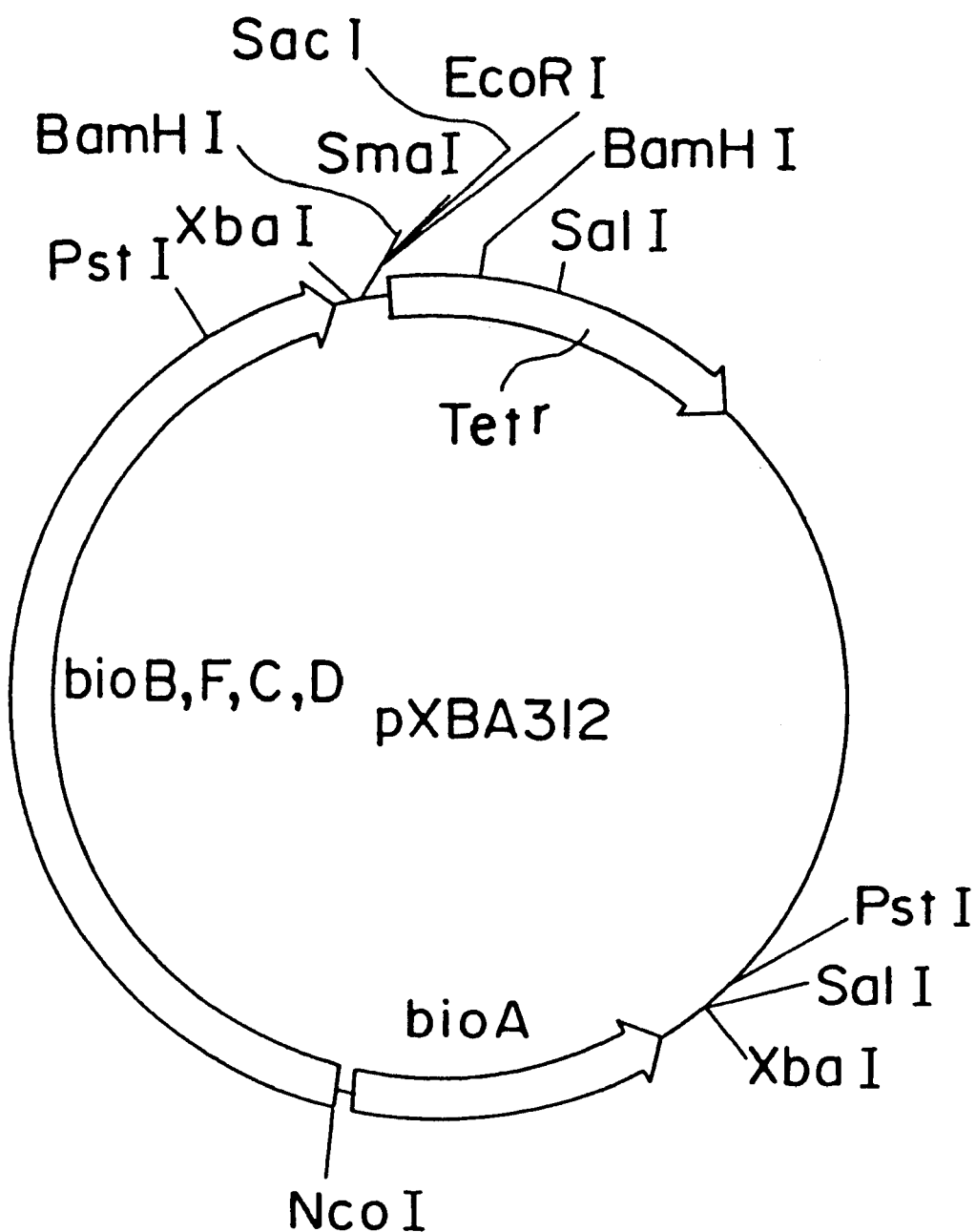
FIG. 2 is a restriction map of DNA of plasmid pXBA 312.

The threonine analogues include, for example, β-hydroxynorvaline.

The biotin operons include, for example, biotin operons derived from microorganisms belonging to the genera Escherichia, Bacillus, and Serratia. The biotin operons derived from microorganisms belonging to the genus Escherichia include biotin operons derived from *Escherichia coli* (JP-A 61-202686, etc.). The five genes bioA, bioB, bioF, bioC and bioD that are involved in biotin biosynthesis are encoded in the biotin operon. In the invention, part of the biotin operon may be modified. The modified biotin operons include, for example, those wherein at least one base pair of either the base sequence of the regulatory region of the biotin operon or the base sequence near the bioB initiation codon of *Escherichia coli* is mutated as compared with the wild type. The regulatory region of the biotin operon is the base sequence shown in Sequence Listing 1 that is a base sequence of r-strand between bioA and bioB, specifically the base sequence of the region from bp (base pair) -1 to bp -86 shown in FIG. 1 when A of the bio B initiation codon ATG is considered bp 1. The base sequence near the bioB initiation codon is the region from bp 1 to bp 6 when A of the bioB initiation codon ATG is considered bp 1. Specifically, at least one GC pair of upstream bp -53 and bp -5 and downstream bp 4 when A of the bioB initiation codon ATG is considered bp 1 is mutated to an AT pair (JP-A 5-219956).

The plasmid to be used in the invention is a plasmid which can be carried by microorganisms belonging to the genus Escherichia, Bacillus or Serratia and the gene of which can be expressed. The plasmid is preferably a plasmid carried by microorganisms belonging to the genus Escherichia. Examples of the plasmids include pXBA312 (derived from *Escherichia coli* DRK-3323 (pXBA312)(FERM BP-2117), JP-A 2-502065), pXBRP319 (derived from *Escherichia coli* MM44/pXBRP319 (IFO 15721, FERM BP-4724), see Example 1 below), pAT 71 (derived from *Escherichia coli* HB/pAT71 (FERM BP-5668)), and derivatives thereof.

The microorganism of the invention can produce and accumulate biotin. Examples thereof include microorganisms belonging to the genus Escherichia, Bacillus or Serratia, etc. The microorganism is preferably a microorganism belonging to the genus Escherichia such as *Escherichia coli*, preferably *Escherichia coli* HNV148/pXBRP319 (FERM BP-5667, IFO 15894), *Escherichia coli* HB/pAT71 (FERM BP-5668, IFO 15895) obtained in Examples below, etc.

The microorganism resistant to a threonine analogue having a plasmid containing part or whole of the biotin operon is preferably a microorganism resistant to a threonine analogue transformed with a plasmid containing part or whole of the biotin operon.

The microorganism of the invention can be obtained, for example, by providing a parent strain of a microorganism with resistance to a threonine analogue and introducing a plasmid containing part or whole of the biotin operon into the resulting strain resistant to the threonine analogue. The microorganism of the invention can also be obtained by introducing a plasmid containing part or whole of the biotin operon into a parent strain of a microorganism and providing the resulting microorganism with resistance to a threonine analogue. Alternatively, the microorganism can be obtained by providing with resistance to a threonine analogue a parent strain of a microorganism carrying a plasmid containing part or whole of the biotin operon.

As the parent strains, any microorganisms can be used in the invention so long as they can produce and accumulate biotin. Examples of the microorganisms include microorganisms belonging to the genera Escherichia, Bacillus and Serratia. The microorganisms belonging to the genus Escherichia include, for example, microorganisms belonging to *Escherichia coli*, such as *Escherichia coli* IFO 14410, *Escherichia coli* W-3110 (IFO 12713) and its derivative strain *Escherichia coli* DR-85 (JP-A 61-202686), *Escherichia coli* DR-332 (JP-A 62-155081), *Escherichia coli* DRK-3323 (JP-A 2-502065), *Escherichia coli* BM4062 (JP-A 64-500081), *Escherichia coli* MS10/pXBRP319 (IFO 15570, FERM BP-4927) obtained in Reference Examples below, and *Escherichia coli* ANA91/pXBRP319 (IFO 15771, FERM BP-4928) obtained in Reference Examples below. The above *Escherichia coli* IFO 14410 and *Escherichia coli* IFO 12713 are known strains listed in List of Cultures, 9th edition (1992) (published by Institute for Fermentation, Osaka, Japan (IFO)) and available from IFO.

The above *Escherichia coli* MS10/pXBRP319 has been deposited with National Institute of Bioscience and Human-Technology, Agency of Industrial Science and Technology of 1-3, Higashi 1-chome, Tsukuba-shi, Ibaraki-ken, Japan, under the Budapest Treaty under the accession umber of FERM BP-4927 since Dec. 12, 1994.

The above *Escherichia coli* ANA91/pXBRP319 has been deposited with National Institute of Bioscience and Human-Technology, Agency of Industrial Science and Technology of 1-3, Higashi 1-chome, Tsukuba-shi, Ibaraki-ken, Japan, under the Budapest Treaty under the accession umber of FERM BP-4928 since Dec. 12, 1994.

The above *Escherichia coli* HNV148/pXBRP319 has been deposited with National Institute of Bioscience and Human-Technology, Agency of Industrial Science and Technology of 1-3, Higashi 1-chome, Tsukuba-shi, Ibaraki-ken, Japan, under the Budapest Treaty under the accession umber of FERM BP-5667 since Oct. 30, 1995.

The above *Escherichia coli* HB/pAT71 has been deposited with National Institute of Bioscience and Human-Technology, Agency of Industrial Science and Technology of 1-3, Higashi 1-chome, Tsukuba-shi, Ibaraki-ken, Japan, under the Budapest Treaty under the accession umber of FERM BP-5668 since Oct. 30, 1995.

The microorganisms belonging to the genus Bacillus include, for example, microorganisms belonging to *Bacillus sphaericus*. Specific examples thereof include *Bacillus sphaericus* IFO 3525 and its derivative strain *Bacillus sphaericus* NZ-8802 (JP-A 4-11894). The above *Bacillus sphaericus* IFO 3525 is a known strain listed in List of Cultures, 9th edition (1992) (published by IFO) and available from IFO.

The microorganisms belonging to the genus Serratia include microorganisms belonging to *Serratia marcescens*. Specific examples thereof include *Serratia marcescens* Sn 41 and its derivative strain *Serratia marcescens* TA5024 (JP-A 2-27980), *Serratia marcescens* SB411 and its derivative strain *Serratia marcescens* ET2 , *Serratia marcescens* ETA23 (JP-A 5-199867), etc.

The above microorganisms can be used as such or as mutants thereof. When the microorganisms contain no plasmid containing part or whole of the biotin operon, if necessary, a plasmid containing part or whole of the biotin operon is transformed into the microorganisms at a later step.

The strains resistant to a threonine analogue can be obtained by per se known methods such as treatment with chemicals (e.g., N-methyl-N'-nitro-N-nitrosoguanidine abbreviated as NTG), and ultraviolet irradiation.

Then, a suspension of the resulting mutant cells is inoculated in a culture medium (e.g., agar plate culture medium) containing a threonine analogue in an appropriate concentration, e.g., a concentration which does not allow the growth of the parent strain. The grown colonies are isolated to conveniently obtain the strain resistant to the threonine analogue.

The threonine analogue-resistant strain obtained in the above method is cultured, and the amount of biotin in the culture supernatant is determined to select microorganisms which can accumulate increased amount of biotin.

The plasmid containing part or whole of the biotin operon can be introduced into the microorganism by per se known methods. The plasmid containing part or whole of the biotin operon can be constructed by per se known methods, for example, by DNA cleavage with a restriction enzyme followed by DNA linkage with T4DNA ligase (Molecular Cloning, A laboratory Manual, Cold Spring Harbor Laboratory, 1982).

The host cell can be transformed with the above plasmid by per se known methods. For example, when the host is a bacterium belonging to the genus Escherichia, the host can be transformed by the method described in Molecular Cloning, A Laboratory Manual, Cold Spring Harbor Laboratory, 1982.

The microorganism resistant to a threonine analogue can be obtained by the above method. Such microorganism can be used as it is. If necessary, such microorganism may further subjected to mutagenesis, and modified plasmids may be used.

The microorganism of the invention obtained in the above method is cultured in a medium to produce biotin in the medium.

The medium used for culture in the invention may be liquid or solid so long as it contains nutrition sources that the microorganisms to be used can utilize. For large scale culture, liquid media are preferably used. The medium contains assimilable carbon sources, assimilable nitrogen sources, inorganic materials, trace nutrients, etc. The carbon sources include glucose, lactose, sucrose, maltose, dextrin, starch, mannitol, sorbitol, glycerol, fats and oils (e.g., soybean oil, olive oil, bran oil, sesame oil, lard oil, chicken oil), and various fatty acids (e.g., lauric acid, myristic acid, palmitic acid, stearic acid, oleic acid). The nitrogen sources include meat extract, yeast extract, dried yeast, soybean flour, defatted soybean flour, corn steep liquor, peptone, cottonseed oil, blackstrap molasses, urea, thiourea, ammonia, and ammonium salts (e.g., ammonium sulfate, ammonium chloride, ammonium nitrate, ammonium acetate). In addition, salts including sodium, potassium, calcium, magnesium, etc., salts with metals such as iron, manganese, zinc, cobalt, nickel, etc., salts of inorganic acids such as phosphoric acid, boric acid, etc., salts of organic acids such as acetic acid, propionic acid, etc., can appropriately be used. In addition, amino acids (e.g., glutamic acid, aspartic acid, alanine, lysine, valine, methionine, proline), peptide (e.g., dipeptide, tripeptide), vitamins (e.g., vitamins $B_1$, $B_2$, $B_{12}$, C, nicotinic acid), nucleic acids (e.g., purine, pyrimidine and derivatives thereof), etc., can also be used. In order to control the pH in the medium, inorganic or organic acids, alkalis, etc., can be added. Appropriate amounts of oils and fats, surfactants, etc., can be used as antifoaming agents. The pH of the medium is preferably about 4 to 10, more preferably about 6 to 9.

The culture is any one of stationary culture, shaking culture, and aerobic and agitating culture. Aerobic and agitating culture is preferred for large scale culture. The temperature for culture is 15 to 42° C., preferably 30 to 37° C. The culture time varies with the culture conditions, but is normally 1 to 10 days, preferably 2 to 4 days.

The culture is conducted by per se known methods such as batch culture, and fed-batch culture.

The resulting culture broth is centrifuged, and the amount of biotin accumulated in the supernatant is determined by per se known methods such as bioassay using *Lactobacillus plantarum* as a test microorganism (The Vitamins, vol. 7, p. 303 (1967); Vitamins, Experimental Procedures (II), p. 475, edited by Japan Vitamin Society (1985); etc.).

The microorganism is cultured by the above method to produce and accumulate biotin in the culture, and then biotin is collected from the culture. Because the biotin thus produced is present mainly in the culture filtrate, it is advantageous to separate the culture to obtain the culture filtrate and cells by per se known methods (e.g., filtration, centrifugation), and separate and purify biotin from the resulting filtrate. Alternatively, biotin can be purified directly from the culture broth.

The separation and purification can be carried out by per se known methods using difference in solubility in an appropriate solvent, precipitation from a solution, difference in precipitation rates, difference in various absorbance affinity, ion-exchange chromatography using ion-exchangers, concentration under reduced pressure, lyophilization, crystallization, recrystallization, drying, etc. These techniques can be used alone or in an appropriate order of their combination.

Biotin obtained by the invention can be used as raw materials for medicaments, cosmetics, etc., feed additives, etc.

The following reference examples and examples further illustrate the invention in detail, but are not to be construed to limit the scope of the invention. All the percents (%) regarding the medium is W/V percents (W/V%).

*Escherichia coli* MS10/pXBRP319 and *Escherichia coli* ANA91/pXBRP319 obtained in the following reference examples have been deposited at Institute for Fermentation, Osaka, Japan (IFO) since Dec. 2, 1994 under the Accession Numbers IFO 15770 and IFO 15771, respectively, and at National Institute of Bioscience and Human-Technology, Agency of Industrial Science and Technology (NIBH), Tsukuba, Japan since Dec. 12, 1994 under the Accession Numbers FERM BP-4927 and FERM BP-4928, respectively.

*Escherichia coli* HNV148/pXBRP319 and *Escherichia coli* HB/pAT71 obtained in the following examples have been deposited at NIBH since Oct. 30, 1995 under the Accession Numbers FERM BP-5667 and FERM BP-5668, respectively.

Reference Example 1

(1) Plasmid pXBA 312 (see FIG. 2) isolated from *Escherichia coli* DRK-3323/pXBA 312 (FERM BP-2117) (JP-A 2-502065) was cleaved with the restriction enzyme EcoRI, partially digested with PstI, and subjected to agarose gel electrophoresis and electroelution to isolate an EcoRI-PstI fragment (6.0 Kbp) containing the full-length biotin operon. The resulting EcoRI-PstI fragment of pXBA 312 was ligated with an EcoRI-PstI fragment (3.6 Kbp) of plasmid pBR 322 to obtain plasmid pXBA 319.

Plasmid pMW 119 (Nippon Gene, Japan) was cleaved with the restriction enzymes AatII and AvaI, and subjected to agarose gel electrophoresis and electroelution to obtain an AatII-AvaI fragment (0.4 Kbp). Then, both ends of the AatII-AvaI fragment were made blunt ends with a blunting kit (Takara Shuzo Co., Ltd., Japan). The resulting fragment was ligated to SmaI site of PXBR 319 to obtain plasmid pXBRP 319.

(2) Plasmid PXBRP 319 obtained in above (1) was transformed into an excellent strain obtained by mutagenesis treatment of *Escherichia coli* IFO 14410 (obtained from Institute for Fermentation, Osaka, Japan) with NTG. The resulting strain was further subjected to mutagenesis with NTG to isolate various drug-resistant strains. A strain producing a large amount of biotin was selected from the drug-resistant strains to obtain *Escherichia coli* MM44/pXBRP 319 (FERM BP-4724).

(3) *Escherichia coli* MM44/pXBRP 319 obtained in above (2) was inoculated in 2×YT medium (20 ml) containing yeast extract 10 g/L, peptone 16 g/L and sodium chloride 5 g/L, and subjected to shaking culture at 37° C. for 16 hours. The resulting culture solution (0.2 ml) was transferred to 2×YT medium (20 ml), and subjected to shaking culture at 37° C. for 6 hours. The resulting culture was centrifuged, and the collected cells were rinsed twice with TM buffer (maleic acid 5.08 g/L, Tris 6.05 g/L, pH 6.0). The rinsed cells were suspended in TM buffer containing 200 μg/ml of NTG, and subjected to mutagenesis at 37° C. for 25 minutes. The treated cells were collected by centrifugation and rinsed twice with TM buffer, and suspended in the same buffer. The resulting suspension was inoculated in an agar plate of M9 minimal medium containing 1 mg/ml β-chloro-D-alanine, 4 μg/ml thiamine hydrochloride and 20 μg/ml Casamino acid, and allowed to stand at 37° C. for 5 days to obtain colonies of strains resistant to β-chloro-D-alanine. One of the strains was selected to obtain *Escherichia coli* BD10/pXBRP 319 (FERM BP-4725).

(4) *Escherichia coli* BD10/pXBRP 319 (FERM BP-4725) obtained in above (3) was subjected to mutagenesis with NTG, and various drug-resistant strains were selected. A strain producing a large amount of biotin was selected to obtain *Escherichia coli* MS10/pXBRP 319.

(5) *Escherichia coli* MS10/pXBRP 319 obtained in above (4) was inoculated in 2×YT medium (20 ml) containing yeast extract 10 g/L, peptone 16 g/L and sodium chloride 5 g/L, and subjected to shaking culture at 37° C. for 16 hours. The resulting culture solution (0.2 ml) was transferred to 2×YT medium (20 ml), and subjected to shaking culture at 37° C. for 6 hours. The resulting culture broth was centrifuged, and the collected cells were rinsed twice with TM buffer (maleic acid 5.08 g/L, Tris 6.05 g/L, pH 6.0). The rinsed cells were suspended in TM buffer containing 200 μg/ml of NTG, and subjected to mutagenesis at 37° C. for 25 minutes. The treated cells were collected by centrifugation and rinsed twice with TM buffer, and suspended in the same buffer. The resulting suspension was inoculated in an agar plate of M9 minimal medium containing 30 μg/ml 6-aminonicotinamide, 4 μg/ml thiamine hydrochloride and 20 μg/ml Casamino acid, and allowed to stand at 37° C. for 5 days to obtain colonies of strains resistant to 6-aminonicotinamide. One of the strains was selected and was designated as *Escherichia coli* ANA91/pXBRP319 (FERM BP-4928).

Reference Example 2

*Escherichia coli* ANA91/pXBRP319 obtained in Reference Example 1 was grown at 37° C. for 16 hours in a 200 ml creased flask containing a seed medium (pH 7.1, 30 ml) composed of glucose 2%, calcium carbonate 1%, corn steep liquor 4%, ammonium sulfate 0.4%, $KH_2PO_4$ 0.1%, $K_2HPO_4$ 0.2% and $MgSO_4.7H_2O$ 0.01% on a rotary shaker. The resulting culture (0.6 ml) was transferred to a 200 ml creased flask containing a main medium (pH 7.1, 30 ml) composed of glucose 5%, corn steep liquor 5%, ammonium sulfate 0.2%, DL-alanine 0.3%, $KH_2PO_4$ 0.1%, $K_2HPO_4$ 0.2%, $MgSO_4.7H_2O$ 0.01%, $FeSO_4.7H_2O$ 0.001% $MnSO_4.4-6H_2O$ 0.001% and thiamine hydrochloride 0.002%, and grown at 37° C. for 30 hours on a rotary shaker at 220 rpm. After completion of the cultivation, the culture was centrifuged. The quantitative analysis of biotin in the culture supernatant showed that 160 mg/ml biotin was accumulated.

Example 1

*Escherichia coli* ANA91/pXBRP 319 obtained in Reference Example 1 was inoculated in 2×YT medium (20 ml) containing yeast extract 10 g/L, peptone 16 g/L and sodium chloride 5 g/L, and subjected to shaking culture at 37° C. for 16 hours. The resulting culture solution (0.2 ml) was transferred to 2×YT medium (20 ml), and subjected to shaking culture at 37° C. for 6 hours. The resulting culture broth was centrifuged, and the collected cells were rinsed twice with TM buffer (maleic acid 5.08 g/L, Tris 6.05 g/L, pH 6.0). The rinsed cells were suspended in TM buffer containing 200 μg/ml of NTG, and subjected to mutagenesis at 37° C. for 25 minutes. The treated cells were collected by centrifugation and rinsed twice with TM buffer, and suspended in the same buffer. The resulting suspension was inoculated in an agar plate of M9 minimal medium containing 2 g/L β-hydroxynorvaline, and allowed to stand at 37° C. for 5 days to obtain colonies of strains resistant to β-hydroxynorvaline. One of the strains was selected and was designated as *Escherichia coli* HNV148/pXBRP319 (FERM BP-5667, IFO 15894).

Example 2

*Escherichia coli* HNV148/pXBRP319 obtained in Example 1 was grown at 37° C. for 16 hours in a 200 ml creased flask containing a seed medium (pH 7.1, 30 ml) composed of glucose 2%, calcium carbonate 1%, corn steep liquor 4%, ammonium sulfate 0.4%, $KH_2PO_4$ 0.1%, $K_2HPO_4$ 0.2% and $MgSO_4.7H_2O$ 0.01% on a rotary shaker at 220 rpm. The resulting culture (0.6 ml) was transferred to a 200 ml creased flask containing a main medium (pH 7.1, 30 ml) composed of glucose 5%, corn steep liquor 5%, calcium carbonate 2%, ammonium sulfate 0.2%, DL-alanine 0.3%, $KH_2PO_4$ 0.1%, $K_2HPO_4$ 0.2%, $MgSO_4.7H_2O$ 0.01%, $FeSO_4.7H_2O$ 0.003%, $MnSO_4.4-6H_2O$ 0.003% and thiamine hydrochloride 0.002%, and grown at 37° C. for 30 hours on a rotary shaker at 220 rpm. After completion of the cultivation, the culture was centrifuged. The biotin accumulation in the resulting culture supernatant was quantified by the bioassay using *Lactobacillus plantarum* IFO 3070 as a test microorganism, and found to be 175 mg/L. In contrast, when the parent strain was cultured under the same conditions, the biotin accumulation was only 160 mg/L.

Example 3

*Escherichia coli* HNV148/pXBRP319 obtained in Example 1 was grown at 37° C. for 16 hours in a 500 ml creased flask containing a seed medium (pH 7.1, 125 ml) composed of glucose 2%, calcium carbonate 1%, corn steep liquor 4%, ammonium sulfate 0.4%, $KH_2PO_4$ 0.1%, $K_2HPO_4$ 0.2%, $MgSO_4.7H_2O$ 0.01%, $FeSO_4.7H_2O$ 0.05%, thiamine hydrochloride 0.002% and tetracycline hydrochloride 0.0012% on a rotary shaker at 210 rpm. The total amount of the culture thus obtained was transferred to a 5 liter jar. fermentor containing a main medium (pH 7.1, 2.5 L) composed of glucose 3%, corn steep liquor 6%, ammonium sulfate 0.2%, $KH_2PO_4$ 0.1%, $K_2HPO_4$ 0.2%, $MgSO_4.7H_2O$ 0.02%, DL-alanine 0.3%, $MnSO_4.4-6H_2O$ 0.003%, $FeSO_4.7H_2O$ 0.003%, $Fe_2(SO_4)_3.nH_2O$ 0.02%, thiamine hydrochloride 0.002%, 25% ammonia water 1.6 ml/L and Actocoal (an antifoaming agent manufactured by Takeda Chemical Industries, Ltd.) 0.02%, and grown at 37° C. at an aeration rate of 2.5 L/minute. The agitation speed was increased from 550 to 850 rpm in proportion to the amount of the cells. An aqueous solution of glucose (66.7%) was continuously added so that the glucose concentration was in the range of 0.1 to 0.5%. During the cultivation, 25% ammonia water was added to maintain the pH in the range of 6.5 to 7.0. If necessary, Actocoal was added for antifoaming. The cultivation for 72 hours gave a culture containing biotin (710 mg/L).

Example 4

(1) Plasmid pAMP72 (JP-A 5-219956) was completely digested with the restriction enzymes NcoI and EcoT22I, and a 1 kb fragment containing a biotin operon promoter was isolated and recovered by agarose gel electrophoresis. Meanwhile, pXBRP 319 was completely digested with NcoI and EcoT22I in the same manner, and an about 10 kb fragment was recovered. The about 10 kb fragment was ligated with the above 1 kb fragment to obtain plasmid pXBRP71.

(2) The plasmid pXBRP 71 obtained in above (1) was completely digested with the restriction enzymes EcoRI and SalI and subjected to agarose gel electrophoresis to obtain a 7 kb fragment containing a biotin operon.

Meanwhile, plasmid pBR 322 (manufactured by Takara Shuzo Co., Ltd. Japan) was completely digested with the restriction enzyme AvaI, precipitated with ethanol, and made blunt ends with a blunting kit (manufactured by Takara Shuzo Co., Ltd. Japan). After inactivation with heat, the resulting fragment was completely digested with the restriction enzyme EcoRI, and separated by agarose gel electrophoresis to obtain a 1.4 kb fragment containing a tetracycline-resistant gene. Plasmid pSTV28 (manufactured by Takara Shuzo Co., Ltd. Japan) was completely digested with the restriction enzymes XmnI and SalI to obtain a 1.1 kb fragment containing a replication origin. The three fragments thus obtained were ligated to make plasmid pAT71.

(3) *Escherichia coli* HNV148/pXBRP319 was subcultured to obtain *Escherichia coli* HNV148 in which plasmid pXBRP319 had been removed. The resulting strain HNV 148 was inoculated in an agar plate of M9 minimal medium containing no thiamine, and allowed to stand at 37° C. for 4 days to obtain thiamine—non-requisite strains. One of these strains was selected and designated as *Escherichia coli* HB.

(4) Plasmid pAT71 obtained in above (2) was introduced into *Escherichia coli* HB obtained in above (3) to obtain *Escherichia coli* HB/pAT71 (IFO 15895).

Example 5

*Escherichia coli* HB/pAT71 obtained in Example 4 was grown at 37° C. for 16 hours in a 200 ml creased flask containing a seed medium (pH 7.1, 30 ml) composed of glucose 2%, calcium carbonate 1%, corn steep liquor 4%, ammonium sulfate 0.4%, $KH_2PO_4$ 0.1%, $K_2HPO_4$ 0.2% and $MgSO_4.7H_2O$ 0.01% on a rotary shaker at 220 rpm. The resulting culture (0.6 ml) was transferred to a 200 ml creased flask containing a main medium (pH 7.1, 30 ml) composed of glucose 5%, corn steep liquor 5%, calcium carbonate 2%, ammonium sulfate 0.2%, DL-alanine 0.3%, $KH_2PO_4$ 0.1%, $K_2HPO_4$ 0.2%, $MgSO_4.7H_2O$ 0.01%, $FeSO_4.7H_2O$ 0.003%, $MnSO_4.4$–$6H_2O$ 0.003% and thiamine hydrochloride 0.002%, and grown at 37° C. for 30 hours on a rotary shaker at 220 rpm. After completion of the cultivation, the culture was centrifuged. The biotin accumulation in the resulting culture supernatant was quantified and found to be 200 mg/L.

Example 6

*Escherichia coli* HB/pAT71 obtained in Example 4 was grown at 37° C. for 16 hours in a 500 ml creased flask containing a seed medium (pH 7.1, 125 ml) composed of glucose 2%, calcium carbonate 1%, corn steep liquor 4%, ammonium sulfate 0.4%, $KH_2PO_4$ 0.1%, $K_2HPO_4$ 0.2%, $MgSO_4.7H_2O$ 0.01%, $FeSO_4.7H_2O$ 0.05%, thiamine hydrochloride 0.002% and tetracycline hydrochloride 0.0012% on a rotary shaker at 210 rpm. The total amount of the culture thus obtained was transferred to a 5 liter jar fermentor containing a main medium (pH 7.1, 2.5 L) composed of glucose 3%, corn steep liquor 6%, ammonium sulfate 0.2%, $KH_2PO_4$ 0.1%, $K_2HPO_4$ 0.2%, $MgSO_4.7H_2O$ 0.05%, DL-alanine 0.3%, $MnSO_4.4$–$6H_2O$ 0.003%, $FeSO_4.7H_2O$ 0.003%, $Fe_2(SO_4)_3.nH_2O$ 0.1%, calcium citrate 1%, thiamine hydrochloride 0.002%, 25% ammonia water 1.6 ml/L and Actocoal (an antifoaming agent manufactured by Takeda Chemical Industries, Ltd.) 0.02%, and grown at 37° C. at an aeration rate of 2.5 L/minute. The agitation speed was increased from 550 to 950 rpm in proportion to the amount of the cells. An aqueous solution of glucose (66.7%) was continuously added so that the glucose concentration was in the range of 0.1 to 0.5%. During the cultivation, 25% ammonia water and 30% potassium hydroxide were added to maintain the pH in the range of 6.5 to 7.0. If necessary, Actocoal was added for antifoaming. At 24 to 72 hours after the beginning of the culture, 1.25% ferric citrate (300 ml) was fed. The cultivation for 82 hours in this manner gave a culture containing biotin (970 mg/L).

As described above, the microorganism of the invention has excellent biotin-productivity. Culturing the microorganism can produce a large amount of biotin.

What is claimed is:

1. An isolated microorganism resistant to β-hydroxynorvaline having a nucleic acid sequence which codes for biotin, said microorganism belonging to the genus Escherichia, Bacillus or Serratia, and produces biotin at a higher yield than a parent strain of said microorganism.

2. An isolated microorganism resistant to β-hydroxynorvaline comprising a plasmid containing all or part of an *Escherichia coli* biotin operon, said microorganism being *Escherichia coli*.

3. The microorganism according to claim 2, which produces biotin at a higher yield than a parent strain of said microorganism.

4. The microorganism according to claim 2, which is *Escherichia coli* MS10/pXBRP 319 (FERM BP-4927) or *Escherichia coli* ANA91/pXBRP319 (FERM BP-4928).

5. The microorganism according to claim 1, which is *Escherichia coli* MS10/pXBRP 319 (FERM BP-4927) or *Escherichia coli* ANA91/pXBRP319 (FERM BP-4928).

6. A process for producing biotin, which comprises culturing the microorganism according to claim 1 in a medium to produce biotin, and collecting the biotin.

7. A process for producing biotin, which comprises culturing the microorganism according to claim 2 in a medium to produce biotin, and collecting the biotin.

8. The process according to claim 6, wherein the microorganism is *Escherichia coli* MS10/pXBRP 319 (FERM BP-4927) or *Escherichia coli* ANA91/pXBRP319 (FERM BP-4928).

9. The process according to claim 7, wherein the microorganism is *Escherichia coli* MS10/pXBRP 319 (FERM BP-4927) or *Escherichia coli* ANA91/pXBRP319 (FERM BP-4928).

* * * * *

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
      (A) LENGTH: 114 bases
      (B) TYPE: nucleic acid
      (C) STRANDEDNESS: double
      (D) TOPOLOGY: linear (ii) MOLECULE TYPE: Genomic DNA (vi) ORIGINAL SOURCE:
      (A) ORGANISM: Escherichia coli (xi) SEQUENCE DESCRIPTION: SEQ ID NO: 1:

```
CGTCCGTTGT CATAATCGAC TTGTAAACCA AATTGAAAAG ATTTAGGTTT          50

ACAAGTCTAC ACCGAATTAA CAACAAAAAA CACGTTTTGG AGAAGCCCCA         100

TGGCTCACCG CCCA                                                114
```